(12) United States Patent
Anazawa et al.

(10) Patent No.: US 6,531,044 B1
(45) Date of Patent: Mar. 11, 2003

(54) CAPILLARY ARRAY ELECTROPHORESIS APPARATUS

(75) Inventors: Takashi Anazawa, Kodaira (JP); Keiichi Nagai, Higashi-yamato (JP)

(73) Assignee: Hitachi, Ltd., Tokyo (JP)

( * ) Notice: Subject to any disclaimer, the term of this patent is extended or adjusted under 35 U.S.C. 154(b) by 0 days.

(21) Appl. No.: 09/425,064

(22) Filed: Oct. 25, 1999

(30) Foreign Application Priority Data

Oct. 26, 1998 (JP) .............................................. 10-303614

(51) Int. Cl.$^7$ ....................... G01N 27/26; G01N 27/447
(52) U.S. Cl. .................... 204/603; 204/452; 356/344
(58) Field of Search ................. 204/452, 603; 356/344

(56) References Cited

U.S. PATENT DOCUMENTS

| | | | |
|---|---|---|---|
| 5,312,535 A | | 5/1994 | Waska et al. ............... 204/603 |
| 5,483,075 A | * | 1/1996 | Smith et al. ............. 204/458.1 |
| 5,538,613 A | * | 7/1996 | Brumley et al. ............ 204/612 |
| 5,571,388 A | * | 11/1996 | Patonay et al. ............. 204/461 |
| 6,100,535 A | * | 8/2000 | Mathies et al. .......... 250/458.1 |
| 6,118,127 A | * | 9/2000 | Liu et al. ................. 250/458.1 |
| 6,225,635 B1 | * | 5/2001 | Brewer et al. ........... 250/458.1 |

FOREIGN PATENT DOCUMENTS

| EP | 854362 | * | 7/1998 |
|---|---|---|---|
| JP | 6-138037 | | 5/1994 |

OTHER PUBLICATIONS

Bio/Technology, vol. 6, Jul. 1988, "Optimization of Parameters in a DNA Sequenator Using Fluorescence Detection", H. Kambara et al, pp. 816–821.

Analytical Chemistry, 1990, 62, "High–Speed Separations of DNA Sequencing Reactions by Capillary Electrophoresis", H. Drossman et al, pp. 900–903.

Nature, Vool. 359, Sep. 10, 1992, "Capillary array electrophoresis: an approach to high–speed, high–throughput DNA sequencing", R. Mathies et al, pp. 167–168.

Nature, vol. 361, Feb. 11, 1993, "Multiple–sheathflow capillary array DNA analyzer", H. Kambara et al, pp. 565–566.

Analytical Chemistry, 1994, 66, Simultaneous Monitoring of DNA Fragments SEparated by Electrophoresis in a Multiplexed Array of 100 Capillaries, K. Ueno et al, pp. 1424–1431.

Analytical Chemistry, vol. 68, No. 15, Aug. 1, 1996, "A Capillary Array Gel Electrophresis System Using Multiple Laser Focusing for DNA Sequencing", T. Anazawa et al, pp. 2699–2704.

* cited by examiner

Primary Examiner—Jill Warden
Assistant Examiner—John S. Starsiak, Jr.
(74) Attorney, Agent, or Firm—Mattingly, Stanger & Malur, P.C.

(57) ABSTRACT

The electrophoresis apparatus includes plural capillaries for separating fluorephore-labeled samples by electrophoresis, fluorescence detecting parts provided in a part of these capillaries arranged in the same place for detecting a fluorescence emitted by fluorephore labels when a part of the plural capillaries is scanned and irradiated by a laser beam, and a fluorescence detection system for detecting this fluorescence. The fluorescence detecting parts are scanned and repeatedly irradiated by the laser bean where a scanning period of the fluorescence detecting parts by the laser bean is $t_1$, and the fluorescence is detected by the fluorescence detecting system where an acquisition time of fluorescence signal is $t_2$ ($t_1 \leq t_2$). The laser bean from a laser source is narrowly converged by a light collecting lens, and a galvanomirror is rotated in a rotation directional of the galvanomirror around the rotation axis of the galvanomirror so as to repeatedly scan the fluorescence detecting parts.

10 Claims, 9 Drawing Sheets

CAPILLARY ARRAY ELECTROPHORESIS APPARATUS

BACKGROUND OF THE INVENTION

Field of the Invention

This invention relates to an apparatus for separating and analyzing DNA, RNA and proteins, and in particular relates to a capillary array electrophoresis apparatus for determining the base sequences of DNA and RNA, and measuring the polymorphism of the base sequences of DNA based on the diversity of individual base sequences.

The analysis of DNA and RNA is becoming increasingly important in genetic analysis and medicine including genetic diagnosis and biology. In recent years, in particular, high-speed, high throughput DNA analyzers are being developed in connection with genome analysis plans.

In DNA analysis, a fluorephore-labeled sample is separated according to molecular weight by gel electrophoresis, and the fluorescence of the fluorephore label is detected. In gel electrophoresis, a flat plate gel formed by polymerizing acrylamide between two glass plates separated by an interval of approximately 0.3 mm is widely used (Biotechnology 6, 816 (1988)). A sample injected at the upper end of the flat plate gel is caused to move by electrophoresis towards the lower end while undergoing molecular separation due to a voltage applied between the two ends of the flat plate gel. A position which is electrophoretically at a certain distance is then irradiated by a laser which irradiates the whole electrophoresis path from the side face of the flat plate gel, and the separated components of the fluorephore-labeled sample passing through the laser irradiation part are excited. The fluorescence from the fluorephore-labeled sample is continuously and periodically measured at a fixed time interval. The results are analyzed to determine a DNA base sequence.

Recently, instead of a flat plate gel, a capillary gel, i.e., a polymerized gel in a fused quartz glass capillary tube, has come to be used. Capillary gel electrophoresis is attracting attention as a larger electric field can be applied than in slab gel electrophoresis, thereby permitting high-speed analysis (Analytical Chemistry 62, 900 (1990)). Normally, an on-column fluorescence detection measurement is performed wherein one capillary tube is used, and the vicinity of the lower end of the capillary is irradiated by a laser. The entire outer surface of the capillary has a polyimide coating, and the coating is removed at the position where fluorescence is to be detected so that the glass is exposed to form a window (U.S. Pat. No. 5,312,535). When this window position is irradiated by the laser, separated components of a fluorephore-labeled sample subject to electrophoresis in the capillary tube are excited when they pass through the beam, the fluorescence from the fluorephore-labeled sample is measured, and is then analyzed to determine the DNA base sequence.

However, in the aforesaid on-line column measuring apparatus, there were disadvantages such as considerable scattering of the laser beam on the outer surface of the capillary, moreover the capillary can be used only once and throughput could not be increased. Recently, there have been several reports of high throughput capillary array electrophoresis devices wherein plural capillaries are disposed in an array, and a large number of samples are simultaneously analyzed at high speed.

The first report is a capillary array scanning method (Nature, 359, 167 (1992)). Plural capillaries are irradiated in sequence one at a time, and on-column fluorescence detection is performed. The fluorescence detection positions of the plural capillaries are disposed horizontally in a plane, a laser beam converged by a lens from a perpendicular direction to the plane is irradiated to one capillary in the array, and the fluorescence is detected by a light collecting lens on the side of the laser beam light source. The part of the capillary array in the plane is moved back and forth in a perpendicular direction to the axis of the capillaries, and laser irradiation and fluorescence detection are sequentially performed for each capillary. The laser irradiation system and fluorescence receiving optical system are fixed. A construction is adopted with a common focal point where the position at which the laser beam is most converged in the capillaries and the position of the light source incident on the fluorescence measuring instrument coincide, and each capillary is measured independently.

The second report is a multiple sheath-flow method (Nature, 361, 565–566 (1993), Japanese Patent Laid-Open Hei 06-138037 (Koho)). The sample elution end of a capillary array disposed in a plane is vertically immersed in a buffer solution, sample components separated by gel electrophoresis are eluted from the capillaries into the buffer solution, a part where there are no capillaries is irradiated by a laser, and fluorescence is detected. An arrangement is adopted wherein the buffer solution is made to flow gradually in the electrophoresis direction so that separate components eluted from different capillary gels are not mixed together in the buffer solution, or two components separated in one capillary gel are not mixed in the buffer solution. A buffer solution part where there are no capillaries, in the vicinity of the outlet of the capillary array, is irradiated by the laser. Hence, the problem of scattering of the laser beam on the surface of the capillaries is avoided, components eluted from plural capillaries are excited together, and fluorescence detection is performed simultaneously. The fluorescence from all the electrophoresis lanes is detected in one operation by a two-dimensional camera in a perpendicular direction to the plane of the capillary array.

The third report is a laser beam expansion method (Analytical Chemistry, 66, 1424–1431 (1994)). Fluorescence detection parts of plural capillaries are arranged horizontally in a plane, and a laser beam is irradiated at an angle of 45° relative to the axis of the capillaries. The laser beam is enlarged in the perpendicular direction to the capillary axes by a cylindrical lens, and all the capillaries are irradiated simultaneously. Fluorescence from all the capillaries is detected in one operation by a two-dimensional camera in a perpendicular direction to the plane of the capillary array.

The fourth report is a multiple laser focusing method (Analytical Chemistry, 68, 2699–2704 (1996)). The fluorescence detecting parts of plural capillaries are arranged in a plane, and a laser beam is irradiated from the side of the plane so as to pass through the center of each capillary. As the laser beam is repeatedly converged by the converging action of each capillary and is not dispersed by the capillary array, all the capillaries can be irradiated simultaneously. Fluorescence from all the capillaries is detected in one operation by a two-dimensional camera in a perpendicular direction to the plane of the capillary array.

SUMMARY OF THE INVENTION

In on-column measurement wherein a capillary is directly irradiated by a laser beam and the resulting fluorescence is detected, the reflection of the laser beam from the inner surface and outer surface of the capillary which enters the fluorescence detecting system gives rise to a high level of background light. If a sufficiently converged laser beam is incident perpendicularly to the axis of the capillary and a fluorescence measurement is performed in a perpendicular direction to the plane formed by the laser beam and capillary axis, the intensity of the laser reflection incident on the fluorescence detecting system is of the order of $10^{-3}$ for a laser reflection intensity of 1. If fluorescence detection is performed in the same direction as that of laser incidence, the laser reflection intensity incident on the fluorescence detecting system is of the order of $10^{-2}$. On the other hand, the fraction of laser scattering intensity due to the separating medium packed in the interior of capillary which is incident on the fluorescence detecting system is of the order of $10^{-5}$. In other words, the laser reflection intensity is two to three orders of magnitude larger than the laser scattering intensity, and it is the major component of the background light in fluorescence measurement.

In capillary array scanning, as laser irradiation and fluorescence measurement are performed sequentially for one capillary at a time, the fluorescence detection time for one capillary is less than in ordinary on-column measurement. In the case of an n capillary array, the fluorescence detection time per capillary is a maximum of 1/n, but in practice, a glass part of the capillary through which sample separating components do not pass is also scanned, so this time is less than 1/n. The time interval between adjacent peaks in the sample electrophoresis pattern is smaller the more rapid the analysis, but if it increases to such an extent that the time required for one scan cannot be ignored compared to this time interval, the resolution of the electrophoresis pattern will decrease.

In a capillary array scanning system, there are a large number of moving parts for scanning, and as they move through large distances, the scanning speed is not very high, in addition to which breakdowns often occur. Moreover, as the signal from each capillary is processed separately, i.e., as the signal obtained in one fluorescence detecting time period corresponds to the signal from one capillary, the scanning speed cannot be much increased. Due to these reasons, current scanning speeds are of the order of 1 Hz. Further, as the laser beam is incident perpendicularly to the capillary axis, and fluorescence detection is performed in the same direction as the incidence direction, a large amount of laser light reflected at the capillary surface enters the fluorescence detection system. As described above, this laser reflection intensity is extremely high, so the fluorescence measurement background light increases and the detection sensitivity declines.

The problem of the multiple sheath-flow method is that, in comparison to an on-column fluorescence measurement, the fluorescence intensity obtained from molecular separation components decreases the higher the molecular weight. This problem is due to the following reason. To ensure that separated components eluted into the buffer solution from the lower end of the capillary gel do not mix due to diffusion, etc., in the buffer solution, the buffer solution must constantly be made to flow at a minimum constant rate in the electrophoresis direction. On the other hand, the electrophoresis rate of sample components which move through the capillary gel as their molecular weights are separated, becomes smaller the larger the molecular weight, i.e., the larger the length of DNA base sequences. The lower the electrophoresis rate of the components in the capillary gel compared to the flowrate of buffer solution, the more the sample components are drawn out in the electrophoresis direction when they are eluted into the buffer solution from the capillary gel. As a result, the fluorescence intensity declines, and detection sensitivity decreases.

In the laser beam expansion method, each capillary is irradiated by a uniform laser intensity, so the expansion width of the laser beam in the perpendicular direction to the capillary axis must be greatly increased compared to the width of the capillary array. This is because the intensity distribution of the laser beam is a Gaussian distribution centered on the beam axis. For example, if the laser expansion width is equal to the capillary array width, the laser irradiation intensity of the capillaries at both ends of the capillary array is of the order of 14% of that of the central capillary. To reduce the variation of irradiating laser intensity between capillaries to 10% or less, the laser expansion width must be increased to at least four times the capillary array width. However, the more the laser expansion width is increased, the more the laser irradiating intensity of each capillary decreases, and the more the fluorescence detection sensitivity decreases. To prevent this, a laser source must be used which has higher output than the laser sources which are usually used. This makes the equipment more bulky and costly.

In the multiple laser focusing method, when the laser beam passes through the capillary array, the laser beam is reflected at the outer surface and inner surface of each capillary, and part of this reflected light enters the fluorescence detection system. As described above, this laser reflection intensity is extremely high, so fluorescence measurement background light increases and detection sensitivity falls.

It is therefore an object of this invention to perform an on-column fluorescence measurement wherein all the scanning is performed by the laser beam, and the fluorescence from all the capillaries is measured in one operation without moving the fluorescence detection system, thereby providing a capillary array electrophoresis apparatus wherein the above problems are resolved.

The capillary array electrophoresis apparatus according to this invention comprises plural capillaries for the electrophoretic separation of a fluorephore-labeled sample, fluorescence detecting parts provided in part of the plural capillaries in the same plane for detecting the fluorescence emitted by a fluorephore label irradiated by a laser beam which scans part of the plural capillaries, and a fluorescence detection system for detecting fluorescence.

In a first construction, scanning is performed by the laser beam to repeatedly irradiate the fluorescence detecting part, the scanning period of the laser beam in fluorescence detecting part is $t_1$, and fluorescence is detected by the fluorescence detection system in a fluorescence detection time $t_2$ ($t_1 \leq t_2$). In this construction, the laser beam is irradiated from a direction wherein the maximum value of the angle between the laser beam and the plane in which the capillaries are disposed, is $\theta_0 \leq 90°$, and the fluorescence detection system comprises an objective lens.

In a second construction, if the laser beam is irradiated from a direction wherein the maximum value of the angle between the laser beam and the plane in which the capillaries are disposed, is $\theta_0 \leq 90°$, scanning is performed by the laser beam to repeatedly irradiate the fluorescence detecting part, the scanning period of a laser beam in fluorescence detecting part is $t_1$, and fluorescence is detected by the fluorescence detection system in a fluorescence detection time $t_2$ ($t_2 \leq t_1$) from a direction wherein the angle made with the plane in which the capillaries are disposed, is $\theta_3 \leq 90°$, the relations $t_1 \leq t_2$ and $\theta_0 < \theta_3 - \tan^{-1}(D/2d)$ are satisfied when the diameter of entrance pupil of the fluorescence detection system is D, and the distance between the center position of the entrance pupil and the position at which the capillaries are irradiated by the laser beam is d. In this construction, the fluorescence detection system is provided with an objective lens, the central axis of the objective lens makes an angle of $\theta_3 \leq 90°$ with the plane in which the capillaries are disposed, the diameter of entrance pupil of the objective lens is D, and the focal distance of the objective lens is d=f.

In a third construction, if the laser beam is irradiated from a direction wherein the maximum value of the angle between the laser beam and the plane in which the capillaries are disposed, is $\theta_0 \leq 90°$, scanning is performed by the laser beam to repeatedly irradiate the fluorescence detecting part, the scanning period of the laser beam in fluorescence detecting part is $t_1$, the central axis of the objective lens makes an angle of $\theta_3 \leq 90°$ with the capillary axis, fluorescence is detected by the fluorescence detecting system in a fluorescence detection time $t_2$, and the distance d between the center position of the entrance pupil of the fluorescence detection system and the position at which the capillaries are irradiated by the laser beam is equal to the focal length of the objective lens, the relations $t_1 \leq t_2$ and $\theta_0 < 180° - \theta_3 - \tan^{-1}(D/2f)$ are satisfied where the entrance pupil of the objective lens is D.

In a fourth construction, if the laser beam is irradiated from a direction wherein the maximum value of the angle between the laser beam and the plane in which the capillaries are disposed, is $\theta_0 \leq 90°$, scanning is performed by the laser beam to repeatedly irradiate the fluorescence detecting part, the scanning period of a laser beam in fluorescence detecting part is $t_1$, fluorescence is detected by the fluorescence detecting system in a fluorescence detection time $t_2$ from a direction in which an angle made with the plane in which the capillaries are disposed is $\theta_3 \leq 90°$, the relations $t_1 > t_2$ and $\theta_0 > \theta_3 + \tan^{-1}(D/2d)$ are satisfied where the diameter of the entrance pupil of the objective lens is D, and the distance between the center position of the entrance pupil and the position at which the capillaries are irradiated by the laser beam is d. In this construction, the fluorescence detection system is provided with an objective lens, the central axis of the objective lens makes an angle of $\theta_3 \leq 90°$ with the plane in which the capillaries are disposed, and when the diameter of the entrance pupil of the objective lens is D, and the focal distance of the objective lens is f, d=f.

In all of the above constructions, the fluorescence detecting part may be a transparent liquid or a transparent solid.

The fluorescence detecting parts of the plural capillaries are disposed in a planar arrangement, the laser beam is focused to irradiate one capillary, and the laser beam is made to scan continuously so as to repeatedly irradiate the fluorescence detection position of each capillary in sequence. The laser beam irradiated to each capillary is reflected by the outer surface and inner surface of the capillary, however these reflected beams are not emitted in all directions but only within a limited range. By disposing the effective aperture (entrance pupil) of the fluorescence detection system which measures the fluorescence emitted by a fluorephore label of a sample moving along the capillaries in one operation, so that this aperture lies outside the aforesaid limited range, the reflected beams do not enter the fluorescence detection system. For example, the laser beam may be focused and made to scan continuously from the direction of an angle of 45° relative to the capillary axis, and irradiate the fluorescence detecting position of each capillary in sequence. The fluorescence detection system simultaneously measures the fluorescence from all the capillaries in one operation from a perpendicular direction to the plane of the capillary array.

The light of the laser beam reflected from the capillary surface is emitted in a direction making an angle of 45° to the capillary axis on the other side of the fluorescence detection system, i.e., laser reflection light is no longer incident on the fluorescence detection system. Further, the time required for the laser beam to perform one scan of the fluorescence detection parts of plural capillaries is arranged to be less than the signal (measuring) acquisition time (fluorescence detection time) in continuous fluorescence measurement. In other words, all the capillaries receive at least one laser irradiation and emit fluorescence in one fluorescence detection (exposure) time period. The scanning array electrophoresis apparatus which implements this laser scanning system offers the following advantages compared to the prior art apparatus.

In capillary array scanning systems, it was physically difficult to increase the scanning rate above 1 Hz. In the construction of this invention, scanning is performed only by the laser beam, there are very few moving parts required for scanning, and moving distances such as that of a galvanomirror, for example, are very small, therefore high-speed scanning is possible. Fluorescence detection is performed simultaneously for all capillaries, so the signal processing rate is sufficiently fast and the resolution of the electrophoresis analysis does not decrease. Also, in the construction of this invention, laser beam reflection light does not enter the fluorescence detection system, so the fluorescence measurement background light level is very low and a high sensitivity fluorescence measurement can be made.

In the construction of this invention, the laser beam is directly irradiated to the capillaries and on-column fluorescence measurement is performed, so decrease of signal intensity with long base sequences, which was a problem in the multiple sheath-flow method, does not occur.

In the laser beam expansion method, the intensity distribution of the laser beam is a Gaussian distribution, so the laser irradiation intensity was different between capillaries, but in the construction of this invention, laser beam scanning is performed at a constant rate, so all capillaries are irradiated by the laser at a uniform intensity. Further, the laser beam scanning width and the width of the capillary array may be made to coincide so that there is no wastage of laser output, and fluorescence measurement may be performed with a laser source of normal output.

In the multiple laser focusing method, part of the laser beam light reflected at the capillary surface entered the fluorescence detection system and caused an increase in background light. However, according to this invention, as described above, a construction is adopted wherein reflected light from the laser beam does not enter the fluorescence detection system, so background light is reduced and a high sensitivity fluorescence measurement can be performed.

According to this invention, the scanning period of the laser beam is arranged to be much shorter than the detection (exposure) period of the fluorescence measurement and scanning is performed with the laser beam to irradiate plural capillaries, so all the capillaries can effectively be simultaneously irradiated, and fluorescence from all the capillaries can be measured in one operation. As the optical system is such that the reflected beam and transmitted beam from the laser irradiated to the capillaries do not enter the entrance pupil of the fluorescence detection system, the background light intensity of the fluorescence measurement is greatly reduced, a high sensitivity fluorescence measurement can be made, and high-speed, high throughput analysis is achieved.

The typical features of this invention will now be summarized referring to FIG. 1. The electrophoresis apparatus according to this invention comprises plural capillaries 1 which perform electrophoretic separation of a fluorephore-labeled sample, fluorescence detecting parts provided in part of these plural capillaries disposed in the same plane which detect the fluorescence emitted by the fluorephore label irradiated by a laser beam 3 which scans part of the plural capillaries, and a fluorescence detection system 10 which detects fluorescence. Scanning is performed by the laser beam so as to repeatedly irradiate the fluorescence detecting parts, the scanning period of a fluorescence detecting part is $t_1$, and fluorescence is detected by the fluorescence detecting system in a fluorescence detection time $t_2$ ($t_1 \leq t_2$). The laser beam 3 from a laser source 2 is narrowly collimated by a light collecting lens 4, a galvanomirror 5 is rotated in a rotational direction 7 of the galvanomirror around a galvanomirror rotation axis 6, and the fluorescence detecting parts are thereby repeatedly scanned. A laser reflection beam 8 and transmitted beam do not enter the fluorescence detection system. According to the above construction, the effect of background light is reduced, and a high sensitivity, large dynamic range fluorescence measurement can be performed.

DESCRIPTION OF THE PREFERRED EMBODIMENTS

The construction of the main parts of the capillary electrophoresis apparatus according to the embodiments of this invention will be described referring to FIG. 1—FIG. 8, and the overall construction of the capillary electrophoresis apparatus according to the embodiments of this invention will be described referring to FIG. 9.

Embodiment 1

Figure 1:
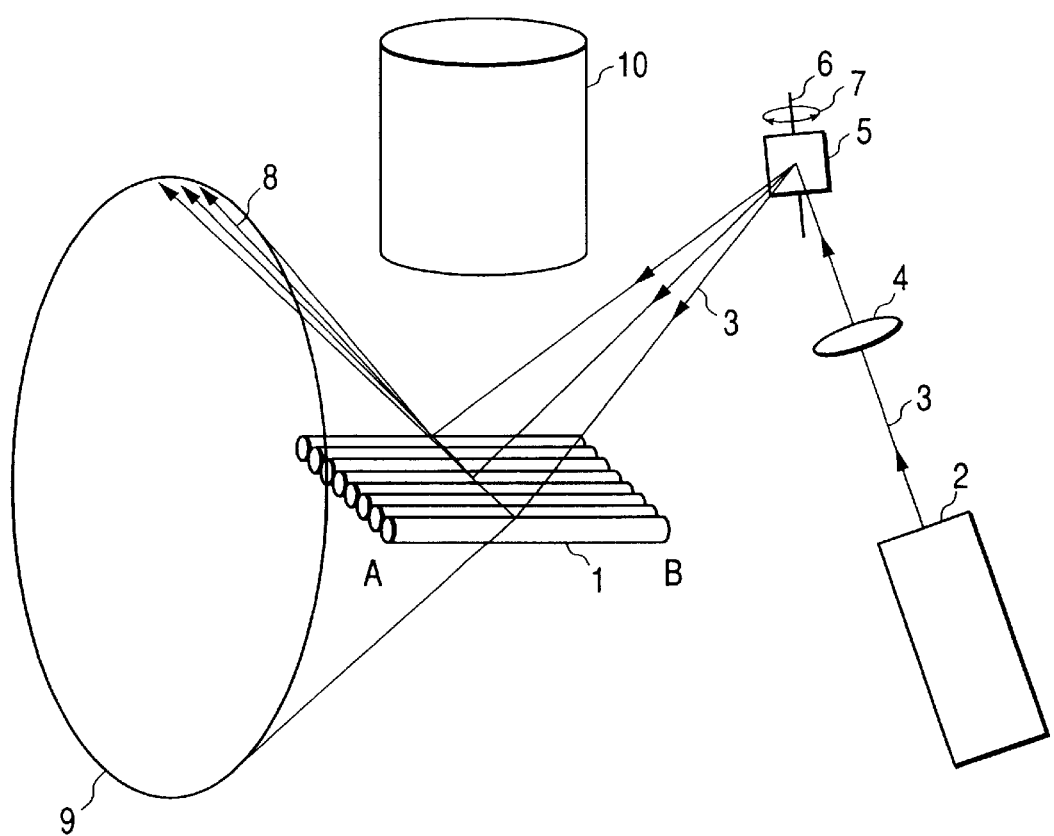
FIG. 1 is a diagram showing the construction of the main parts of a capillary electrophoresis apparatus according to a first embodiment of this invention.

FIG. 1 is a diagram showing the construction of the main parts of a capillary electrophoresis apparatus according to a first embodiment of this invention. Fluorescence detecting parts (polyimide coating removed) of eight capillaries 1 having an outer diameter of 360 μm, inner diameter of 50 μm, overall length of 60 cm and effective length of 50 cm, for detecting fluorescence when scanned by a laser, are horizontally disposed in the same plane (hereafter referred to as capillary array plane). The width of the capillary array of fluorescence detecting parts is 2.88 mm. The interior of the capillary 1 is filled with 5% linear polyacrylamide polymer which is an electrophoresis separating medium, where a fluorephore-labeled sample is electrophoretically separated. FIG. 1 shows only the parts of the capillaries 1 in the vicinity of the fluorescence detecting parts for detecting fluorescence when scanned by the laser beam 3, other parts being omitted (the overall construction of the capillary electrophoresis apparatus will be described referring to FIG. 9). As shown in FIG. 1, the direction of the capillary 1 is referred to as A and the other direction is referred to as B to facilitate understanding of the construction of the apparatus. This invention may also be applied to other conditions where the number of capillaries, outer diameter, inner diameter, length and separating medium are different from those described above.

The laser beam 3 (515 nm, 20 mW) from an Ar ion laser source 2 for exciting fluorescence passes through a light collecting lens 4 (f=100 mm), and is reflected by a galvanomirror 5 to change the direction of the beam. The galvanomirror 5 is free to rotate around its rotation axis 6. The direction of travel of the laser beam 3 is continuously varied by the galvanomirror 5 so that the fluorescence detecting parts of all the capillaries 1 are irradiated in sequence.

The irradiation of the capillaries 1 by the laser beam 3 is set so that the maximum value of the incidence angle of the laser beam 3 on the plane of the capillary array is 45°. Further, the incidence angle of the laser beam 3 on the plane of the capillary array is set to be a maximum when the laser beam 3 irradiates the capillary in the center of the capillary array. Specifically, the setting is such that, when the laser beam 3 irradiates the capillary in the center, a vertical line dropped from one point on the laser beam 3 to the plane of the capillaries intersects with the axis of the capillary in the center.

In the first embodiment, the distance between a position irradiated by the laser beam to the capillaries 1 and the point on the galvanomirror 5 at which the laser beam 3 is reflected (arranged to be about 100 mm) is larger than the width of the capillary array (2.88 mm), so the incidence angle of the laser beam 3 to the axis of each capillary is effectively constant at 45° in the direction B (the incidence angle to the capillaries at the two ends is slightly less than the incidence angle to the capillary in the center, but this difference is very small).

A straight line (scanning line) in the plane of the capillary array formed by joining the points on the capillaries 1 irradiated by the laser is arranged to be perpendicular to the axis of the capillaries 1. The laser beam continuously moves back and forth on this straight line (scanning line) due to the continuous movement of the galvanomirror 5, and repeatedly scans the laser irradiation positions. The laser beam 3 is converged by the light collecting lens 4 to 100 μm or less on the scanning line. The time required for one scan is 0.1 sec.

Figure 2:
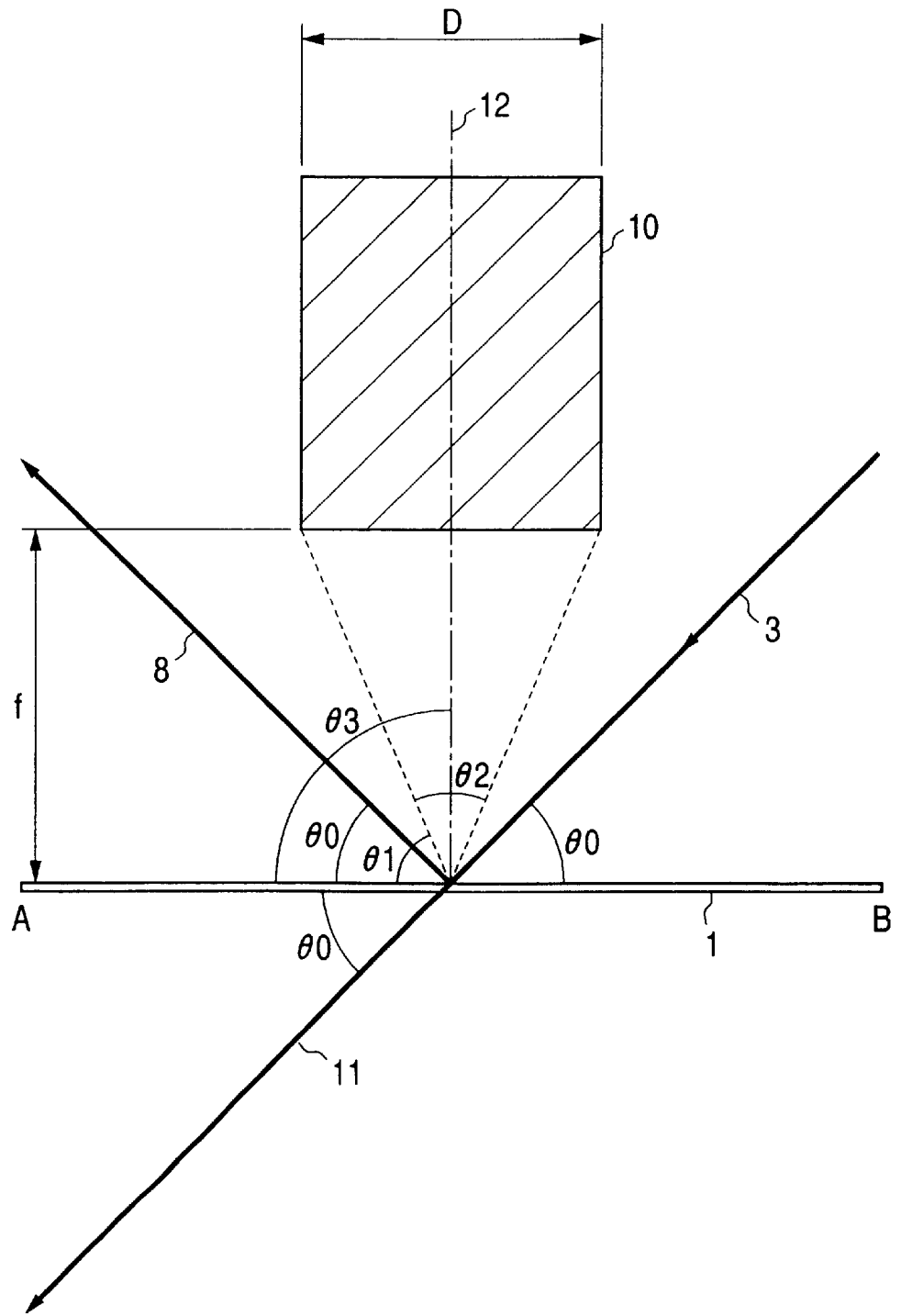
FIG. 2 is a view in vertical section through the plane of a capillary array comprising the axis of a capillary disposed in the center of the capillaries, and showing the main parts of the capillary electrophoresis apparatus according to the first embodiment of this invention.

The laser beam 3 irradiated to the capillaries 1 is partially reflected at the outer surface and inner surface of the capillaries 1, and the remainder is refracted and transmitted through the capillaries 1. As the capillaries 1 are cylindrical in shape, the reflected beam 8 and transmitted beam 11 (the transmitted beam 11 is not shown in FIG. 1, but is shown in FIG. 2) proceed in various directions, but all of the reflected beam 8 and transmitted beam 11 lie on a cone-like curved surface 9 shown in FIG. 1. In other words, the cone-like curved surface 9 is formed by the reflected laser beam 8 and transmitted laser beam 11. The apex of the cone-like curved surface 9 is the laser irradiation position of the capillaries 1, the center axis of the cone-like curved surface 9 coincides with the axis of the capillaries 1, and the apex angle of the cone-like curved surface 9 is twice the laser incidence angle, i.e., 90°. The direction in which the reflected beam 8 has a maximum intensity is on the same side as the laser beam 3 relative to the plane of the capillaries, as shown in FIG. 1, and it makes an angle 45° with the axis of the capillaries in the direction A. The direction in which the transmitted beam 11 has a maximum intensity is on the opposite side of the plane of the capillary array to the incident laser beam 3, and it makes an angle 45° with the axis of the capillaries in the direction A.

The fluorescence emitted from the laser irradiation positions of the capillaries 1 is detected in one operation by the fluorescence detection system perpendicular to the plane of the capillary array and from the same side as that of the laser beam 3. The fluorescence detection system comprises an objective lens 10 which makes the fluorescent light an effectively parallel light flux, a diffraction grating which spectrally disperses the fluorescence, an image forming lens which forms an image, and a two-dimensional camera which detects the image. The image obtained is processed by computer and recorded, and the fluorescence from all the capillaries 1 is measured simultaneously after spectral dispersion. The fluorescence measurement is performed continuously with an exposure time of 0.4 sec and a sampling time of 0.5 sec. As the time required for one laser scan is 0.1 sec, four laser scans are performed in the time of one fluorescence detection (exposure). In other words, all the capillaries 1 are irradiated without fail in one fluorescence detection (exposure) time.

The fluorescence detection system may have other constructions different from that described above. For example, a image splitting prism and spectral filters may be used instead of the diffraction grating as spectroscopic means, or an image-forming diffraction grating may be used instead of the image-forming lens. Whatever the case, it is sufficient if the fluorescence emitted from the plural capillaries 1 is independently and simultaneously detected.

FIG. 1 shows the objective lens 10. If we consider an ordinary fluorescence detection system, the diameter of the entrance pupil of the objective lens 10 represents the entrance pupil of the fluorescence detection system. The entrance pupil of the fluorescence detection system shows the angular range within which light emissions enter the fluorescence detection system to be measured. The most important point is that, as is clear from geometrical optics, none of the reflected beams 8 and transmitted beams 11 on the cone-like curved surface 9 enter the entrance pupil of the fluorescence detection system.

FIG. 2 is a diagram showing the essential parts of a capillary electrophoresis apparatus according to the first embodiment of this invention, and is a sectional view perpendicular to the plane of the capillary array including the axis of the capillary in the center of the capillary array. In other words, FIG. 2 is a sectional view from the direction of the scanning line in FIG. 1. The laser beam 3 incident at an angle of $\theta_0=45°$ to the axis of the capillaries 1 in the direction B, irradiates the capillaries 1, and is split into the reflected beam 8 and transmitted beam 11. Herein, it is assumed that $0°<\theta_0 90°$ (it is assumed that when $\theta_0$ exceeds 90° in FIG. 2, this is an angle in the direction A of the axis of the capillaries 1).

The reflected beam 8 of maximum intensity proceeds at an angle of $\theta_0=45°$ to the axis of the capillaries 1 in the direction A. The transmitted beam 11 of maximum intensity proceeds on an extrapolation of the incident beam 3 at an angle of $\theta_0=45°$ to the axis of the capillaries 1 in the direction A. Other reflected beams 8 and transmitted beams 11 lie within a range of less than 45° to the axis of the capillaries 1 in the direction A. The objective lens 10 of the fluorescence detection system has a diameter of entrance pupil D=40 mm, focal length f=50 mm and F-number F=f/D=1.25. Here, the distance d between the laser irradiation points of the capillaries and the objective lens is made to coincide with the focal distance f so that the fluorescence from the capillaries is made into an effectively parallel light flux by the objective lens 10.

The angle made by a central axis 12 of the objective lens 10, i.e., the central axis 12 of the entrance pupil of the objective lens and the axis of the capillaries 1, is $\theta_3=90°$. Here, it will be assumed that $0°<\theta_3\leq90°$. The entrance pupil angle of the objective lens is $\theta_2=2\times\tan^{-1}(D/2d)=2\times\tan^{-1}(D/2f)=2\times\tan^{-1}(1/2F)=44°$. The angle nearest to the direction A of the axis of the capillaries 1 within the entrance pupil range is $\theta_1=\theta_3-(\theta_2/2)=68°$. As $\theta_0<\theta_1$, the reflected beam 8 does not enter the entrance pupil of the objective lens 10. The incidence angle and reflection angle of the laser beam 3 at capillaries distant from the center of the capillary array are less than $\theta_0$, so this reflected beam 8 also does not enter the entrance pupil.

In general, if $\theta_0<\theta_1$, the reflected beam 8 does not enter the entrance pupil of the fluorescence detection system. In other words, the condition for the reflected beam 8 not to enter the entrance pupil of the fluorescence detection system is $\theta_0<\theta_3-\tan^{-1}(D/2d)$. Due to the above construction, the reflected beam 8 and transmitted beam 11 of the laser beam 3 which is incident to the capillaries 1 do not enter the fluorescence detection system, so background light intensity during fluorescence measurements is greatly reduced. As a result, the detection sensitivity of fluorescence measurements improves, and a widening of dynamic range is obtained.

Embodiment 2

In the first embodiment, the laser beam 3 and fluorescence detection system were situated on the same side with respect to the plane of the capillary array, but in the second embodiment, the laser beam 3 and fluorescence detection system are disposed on opposite sides.

Figure 3:
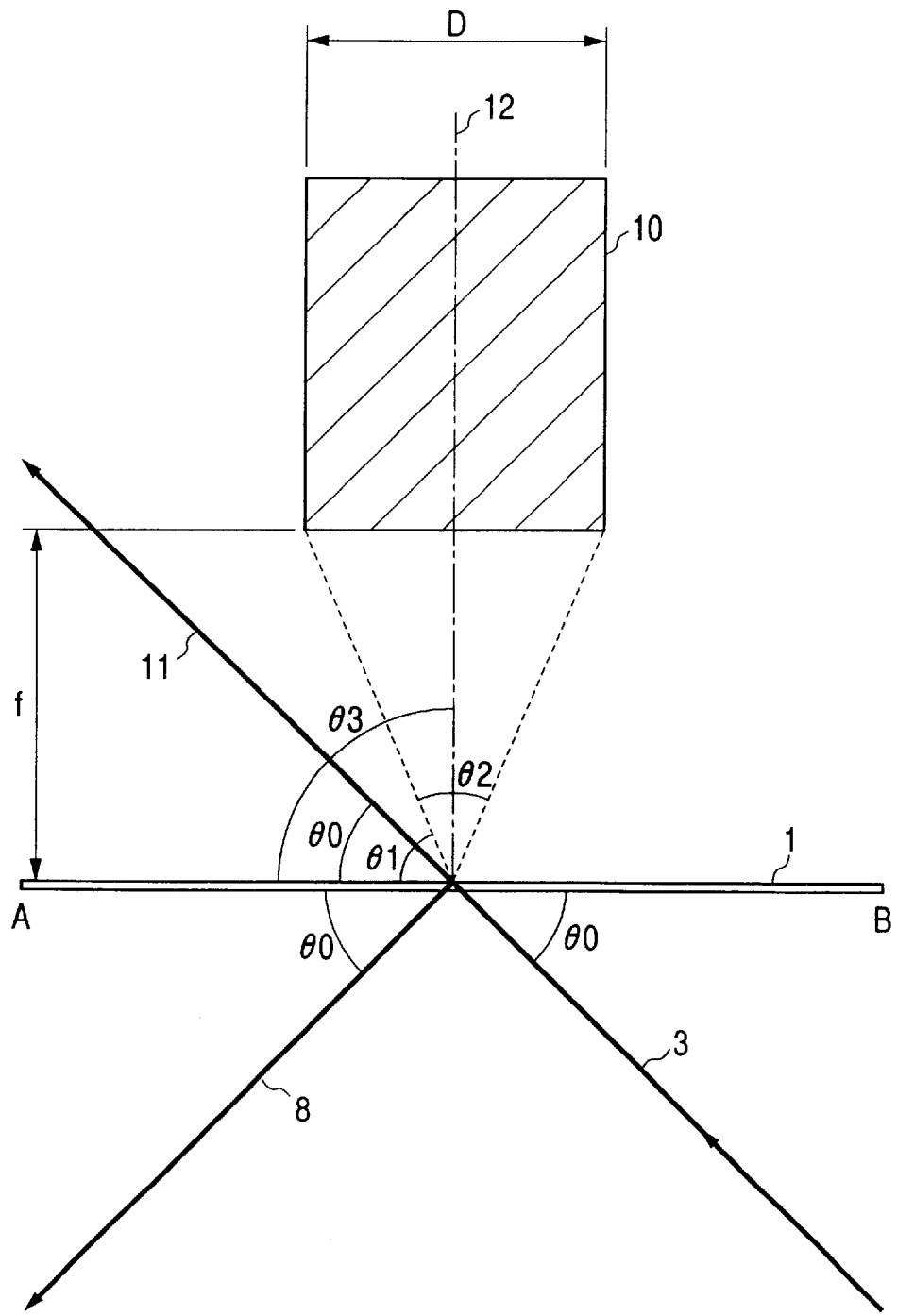
FIG. 3 is a view in vertical section through the plane of a capillary array comprising the axis of a capillary disposed in the center of the capillaries, and showing the main parts of a capillary electrophoresis apparatus according to a second embodiment of this invention.

FIG. 3 is a diagram showing the essential parts of the capillary electrophoresis apparatus according to the second embodiment of the invention, and is a sectional view perpendicular to the plane of the capillary array including the axis of the capillary in the center of the capillary array. The capillaries 1 and fluorescence detection system are the same as in FIG. 2, but the laser beam 3 is disposed on the opposite side of the plane of the capillary array to the fluorescence detection system, and the incidence angle of the laser beam 3 on the capillaries 1 is set to be $\theta_0=45°$ to the axis of the capillaries 1 in the direction B. The remaining conditions are identical to those of the first embodiment. As can be seen from FIG. 3, in this case, if $\theta_0<\theta_3-\tan^{-1}(D/2d)$, the reflected beam 8 and transmitted beam 11 of the laser beam 3 do not enter the entrance pupil of the fluorescence detection system (objective lens 10), and the same effect as that of the first embodiment is obtained.

Embodiment 3

Figure 4:
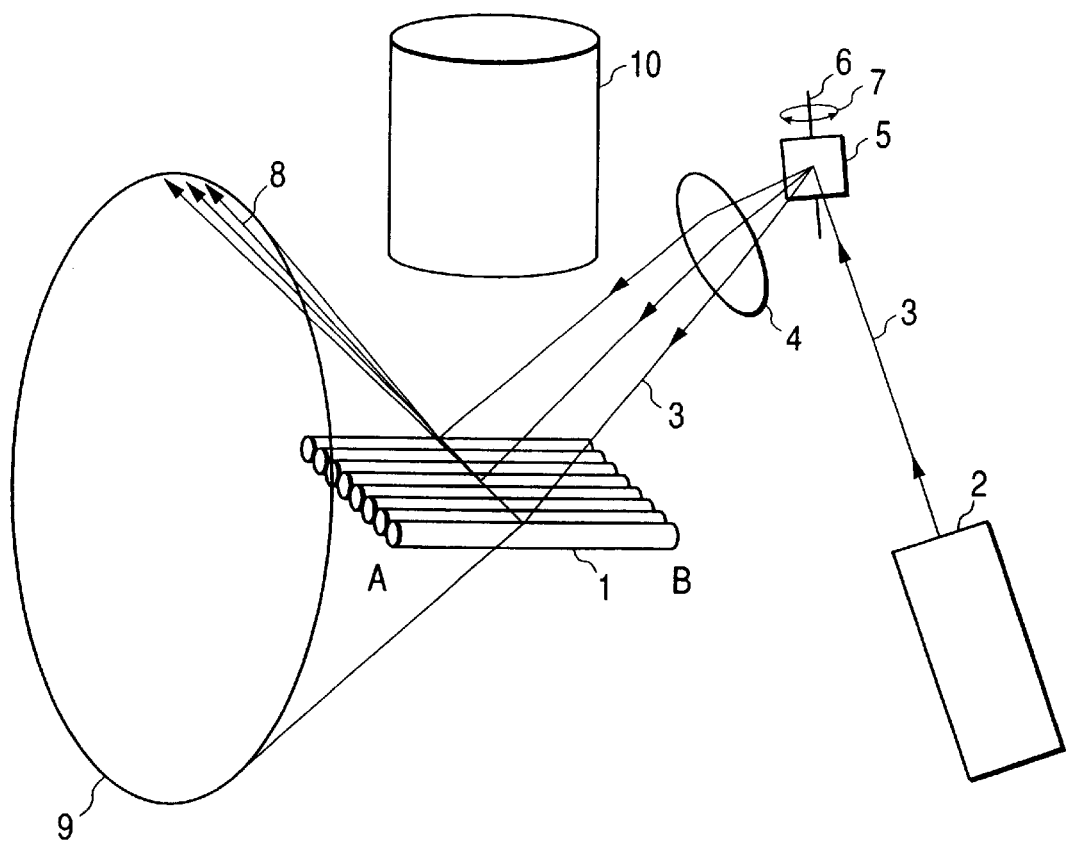
FIG. 4 is a diagram showing the construction of the main parts of a capillary electrophoresis apparatus according to a third embodiment of this invention.

FIG. 4 is a diagram showing the construction of the essential parts of a capillary electrophoresis apparatus according to a third embodiment of this invention. In the first embodiment, the laser source 2, light collecting lens 4 and galvanomirror 5 were arranged in that order, but in the third embodiment, the order of these components is reversed, i.e., laser source 2, galvanomirror 5 and light collecting lens 4. In general, the latter arrangement is more difficult than the former from the viewpoint of design of the optical system, but it has the effect that the beam waist of the laser beam 3 is uniform on the scanning line. Also, as the distance between the scanning line and light collecting lens 4 can be reduced, the light collecting lens 4 of shorter focal length can be used and a narrower beam waist is obtained. In other words, the latter arrangement makes it possible to construct a uniform, highly accurate optical system.

In the construction of FIG. 4, the focal length of the light collecting lens 4 is f=50 mm, and the laser beam diameter on the scanning line is 50 μm or less. If other conditions are identical to those of the first embodiment, an identical effect is obtained.

Figure 5:
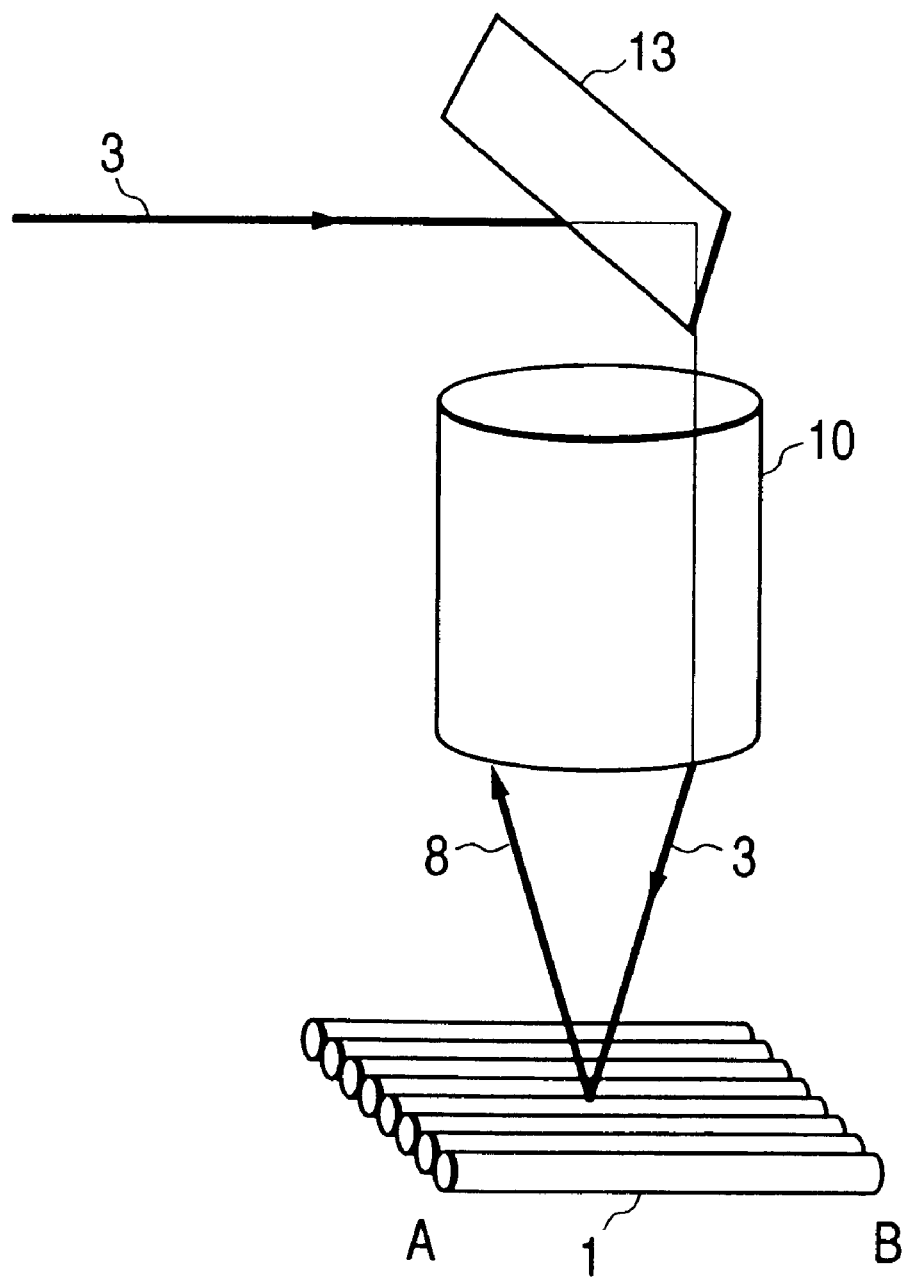
FIG. 5 is a diagram showing the construction of the main parts of a capillary electrophoresis apparatus according to the third embodiment of this invention.

FIG. 5 is another diagram showing the construction of the essential parts of the capillary electrophoresis apparatus according to the third embodiment of this invention wherein, as a variant of the construction, the objective lens 10 and the light collecting lens 4 are combined. The laser beam 3 which has passed via the galvanomirror 5, not shown, is reflected by a dichroic mirror 13, passed through the objective lens 10 to converge it, and irradiates the capillaries 1. As the focal length of the objective lens 10 is f=50 mm, the laser beam width on the scanning line is 50 μm or less. When the galvanomirror 5 is operated, the laser beam irradiating position is moved back and forth on the scanning line so that the laser beam repeatedly irradiates the capillaries 1 one after another. If the central axis 12 (not shown in FIG. 5) of the objective lens 10 makes an angle of $\theta_3=90°$ with the plane of the capillary array, $\theta_0>\theta_1$, so in this case the laser reflected beam will enter the entrance pupil of the fluorescence detection system (objective lens 10).

Figure 6:
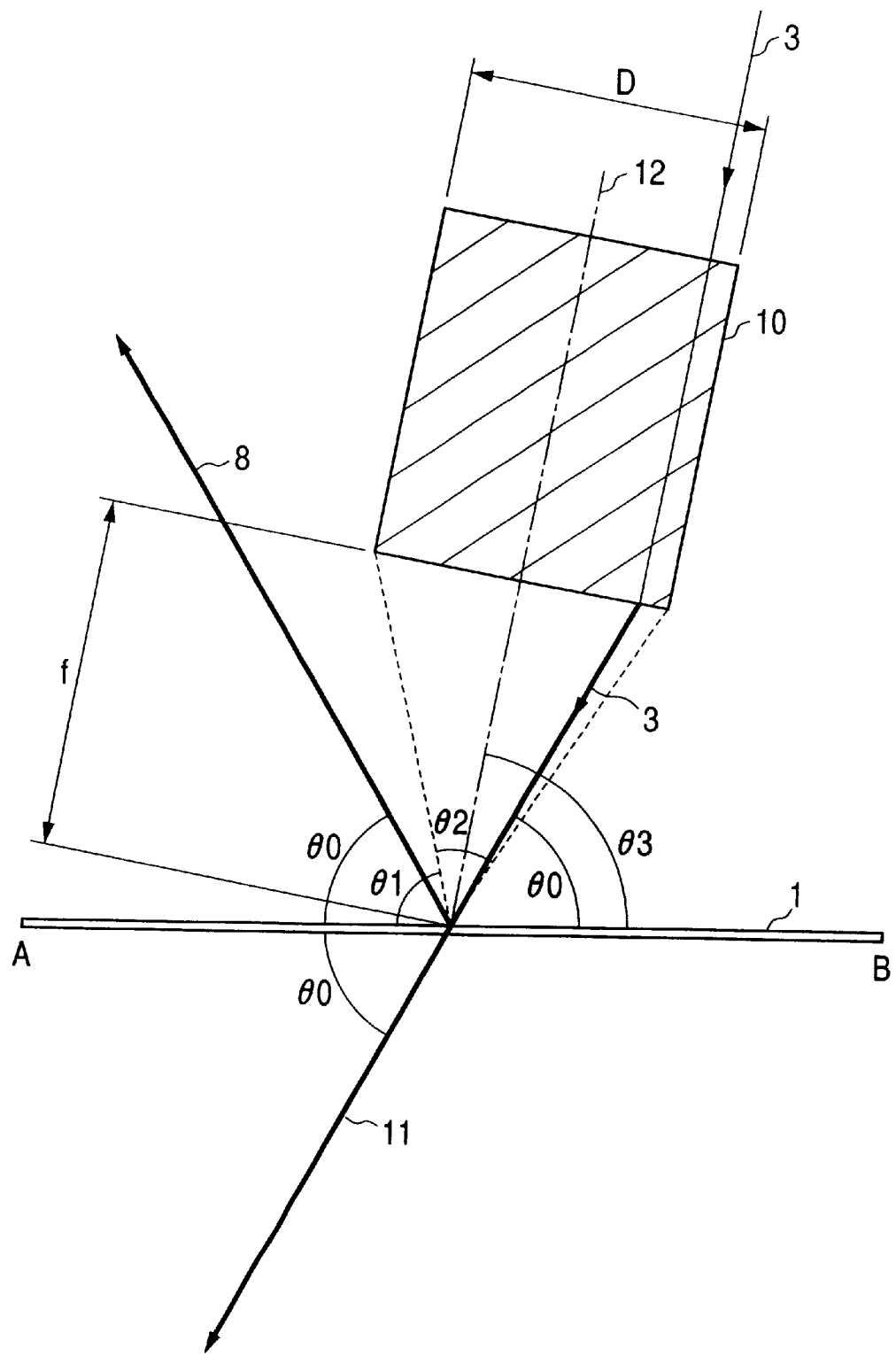
FIG. 6 is a view in vertical section through the plane of a capillary array plane comprising the axis of a capillary disposed in the center of the capillaries, and showing the main parts of the capillary electrophoresis apparatus according to the third embodiment of this invention.

FIG. 6 is another variation showing the essential parts of the capillary electrophoresis apparatus of the third embodiment of this invention, and is a sectional view perpendicular to the plane of the capillary array including the axis of the capillary in the center of the capillary array. As in the case of the first embodiment, the incidence angle of the laser beam 3 on the plane of the capillary array is set to be a maximum when the laser beam 3 irradiates the capillary in the center of the capillary array. Here, as shown in FIG. 6, $\theta_3=80°<90°$. In this case, $\theta_1=180°-\theta_3-(\theta_2/2)=78°$.

Further, to reduce $\theta_0$ as far as possible, $\theta_0 \sim \theta_3-(\theta_2/2)$ is arranged to be 58° by passing the laser beam 3 through the edge of the objective lens 10 as shown in FIG. 6. In this arrangement, $\theta_0<\theta_1$, so the laser reflected beam 8 does not enter the entrance pupil of the fluorescence detection system (objective lens 10), and the same effect as that of the first embodiment is obtained. In general, when a laser beam irradiates capillaries through an objective lens, the laser beam does not enter the fluorescence detection system if $\theta_0<180°-\theta_3-\tan^{-1}(D/2d)$ is satisfied. The dichroic mirror 13 is designed to reflect laser wavelengths and transmit fluorescence wavelengths, and the optical system apart from the above may be designed to the same as that of the first embodiment.

Embodiment 4

In the first embodiment, if the maximum value of the incidence angle of the laser beam 3 on the plane of the capillary array is $\theta_0=90°$, the incident beam 3, reflected beam 8 and transmitted beam 11 are all contained in a plane comprising the laser scanning line perpendicular to the plane of the capillary array and the axis of the capillaries 1.

Figure 7:
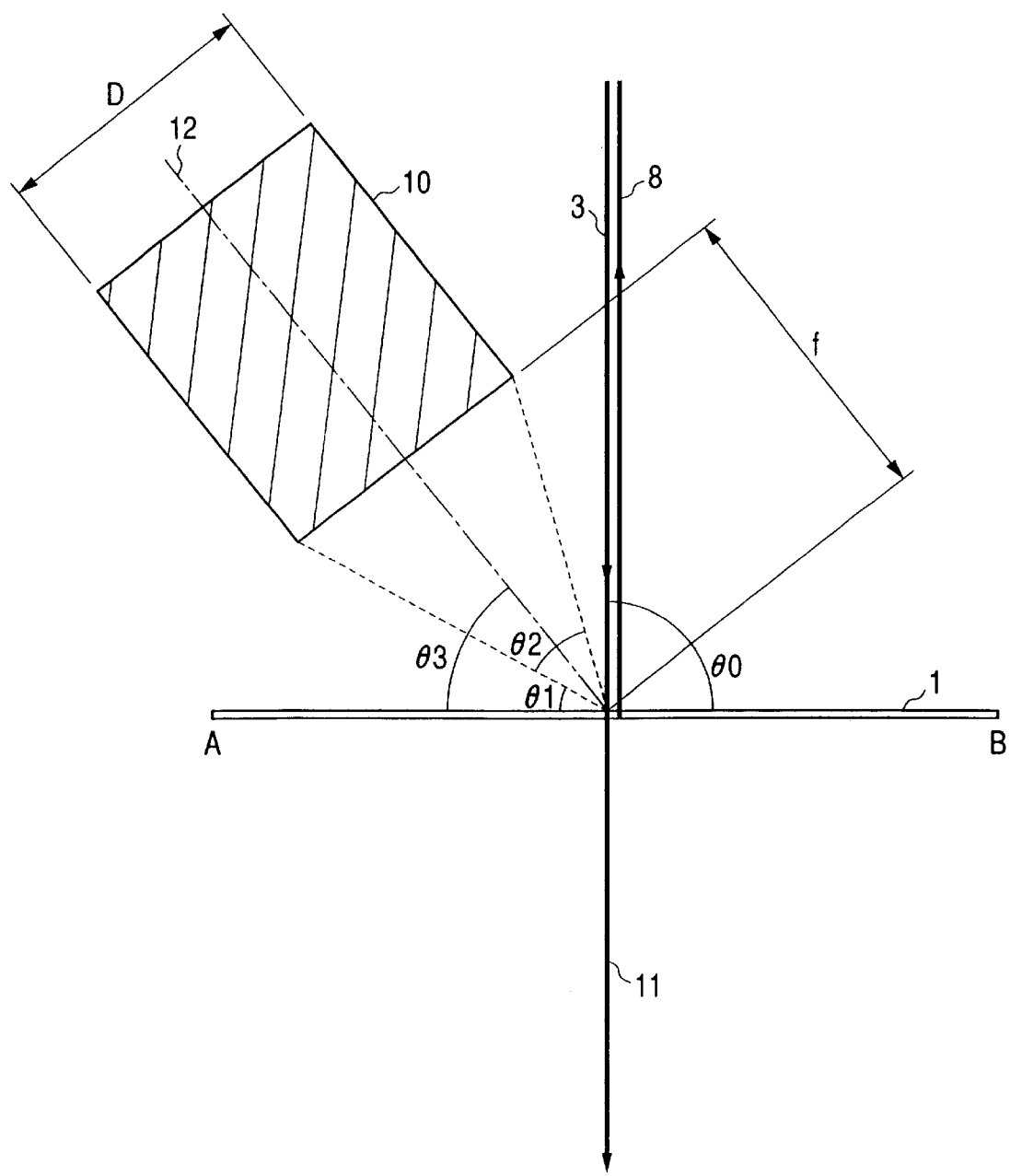
FIG. 7 is a view in vertical section through the plane of a capillary array comprising the axis of a capillary disposed in the center of the capillaries, and showing the main parts of the capillary electrophoresis apparatus according to a fourth embodiment of this invention.

FIG. 7 is a diagram showing the essential parts of a capillary electrophoresis apparatus according to a fourth embodiment of this invention, and is a sectional view perpendicular to the plane of the capillary array including the axis of the capillary in the center of the capillary array. As in the case of the first embodiment, the arrangement is such that the incidence angle of the laser beam 3 on the plane of the capillary array is a maximum when the laser beam irradiates the capillary in the center of the capillary array.

As shown in FIG. 7, if the entrance pupil of the fluorescence detection system (objective lens 10) is inclined to some extent, the reflected beam 8 and transmitted beam 11 of the laser beam 3 do not enter the fluorescence detection system, and the same effect as that of the first embodiment is obtained. The necessary condition is $\theta_0>\theta_1+\theta_2=\theta_3+(\theta_2/2)=\theta_3+\tan^{-1}(D/2d)=\theta_3+\tan^{-1}(D/2f)$. Here, if $\theta_3=40°$, the right-hand side is 62° and the condition is satisfied. The remaining features of the optical system may be the same as those of the first embodiment. Even if $\theta_0<90°$, the same effect is obtained if the above condition is satisfied.

Embodiment 5

In the aforesaid embodiments, the construction is such that the reflected beam from the irradiating laser beam does not directly enter the fluorescence detection system, however it is impossible to avoid laser scattering at the outer surface of the capillary, or to avoid stray light produced by the laser beam colliding with other objects from entering the fluorescence detection system. In the aforesaid embodiments, the space around the irradiation position of the laser 3 on the capillaries 1 was filled with air, but if it is surrounded by a transparent liquid or solid, the reflected laser beam intensity will decrease, the aforesaid laser scattering and stray light will also decrease, and the background light intensity in fluorescence detection will be reduced.

Figure 8:
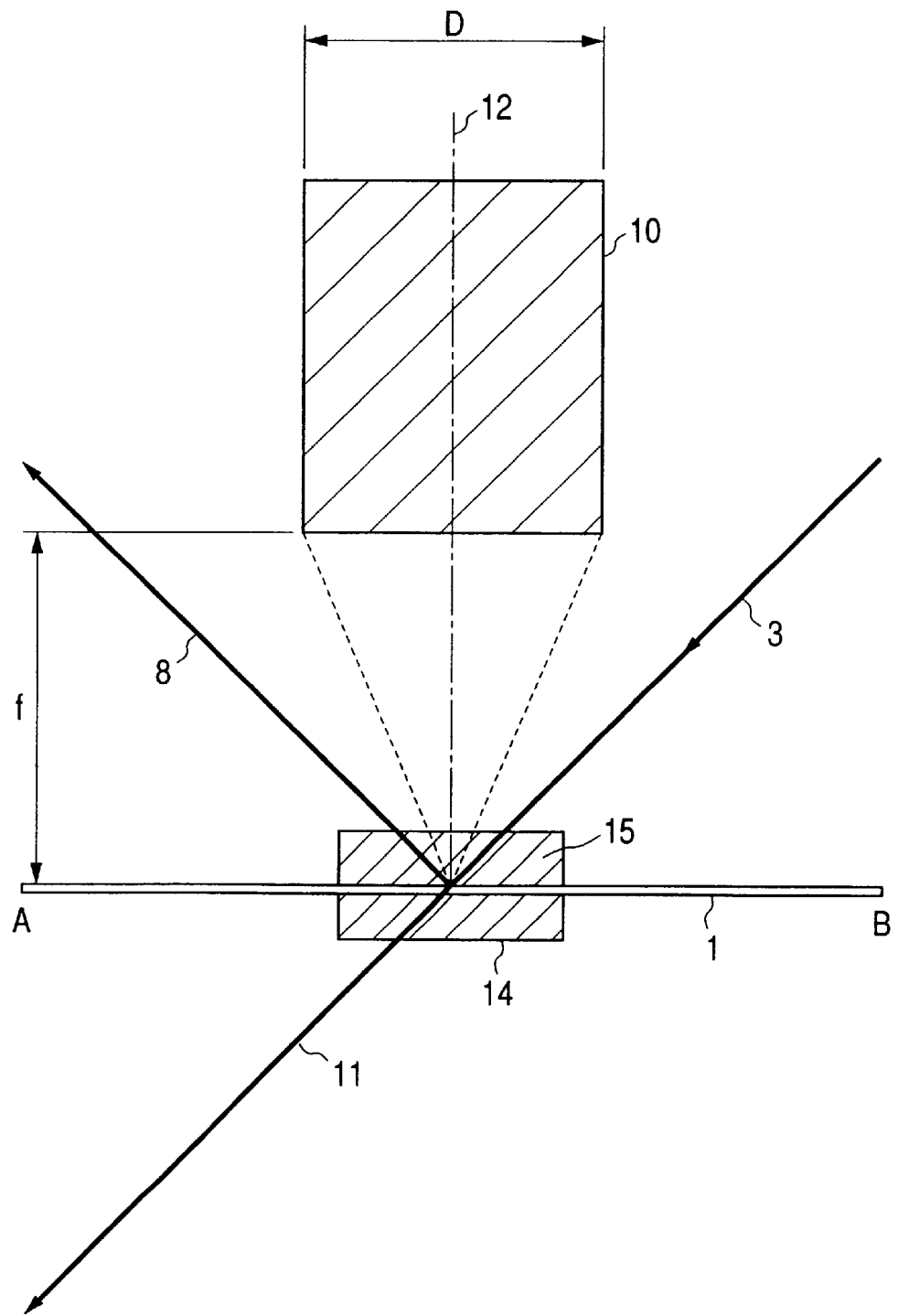
FIG. 8 is a view in vertical section through the plane of a capillary array comprising the axis of a capillary disposed in the center of the capillaries, and showing the main parts of a capillary electrophoresis apparatus according to a fifth embodiment of this invention.

FIG. 8 is a diagram showing the essential parts of a capillary electrophoresis apparatus according to a fifth embodiment of this invention, and is a sectional view perpendicular to the plane of the capillary array including the axis of the capillary in the center of the capillary array. As shown in FIG. 8, in an optical system of identical construction to that of the first embodiment, the irradiation position of the laser beam 3 on the capillaries 1 is situated inside a quartz glass cell 14 filled with pure water 15. Instead of the pure water 15, another transparent liquid may be used, and reduction of laser scattering and stray light is more pronounced the nearer the refractive index of the transparent liquid is to the refractive index of the glass of the capillary material. The same effect is obtained if the space surrounding the irradiation position of the laser beam 3 on the capillaries 1 is filled with a transparent solid having a refractive index near to that of the glass of the capillary material.

In the aforesaid embodiments, the construction of the principal components of the capillary electrophoresis apparatus was described. The overall construction of the capillary array electrophoresis apparatus of this invention will now be described.

Figure 9:
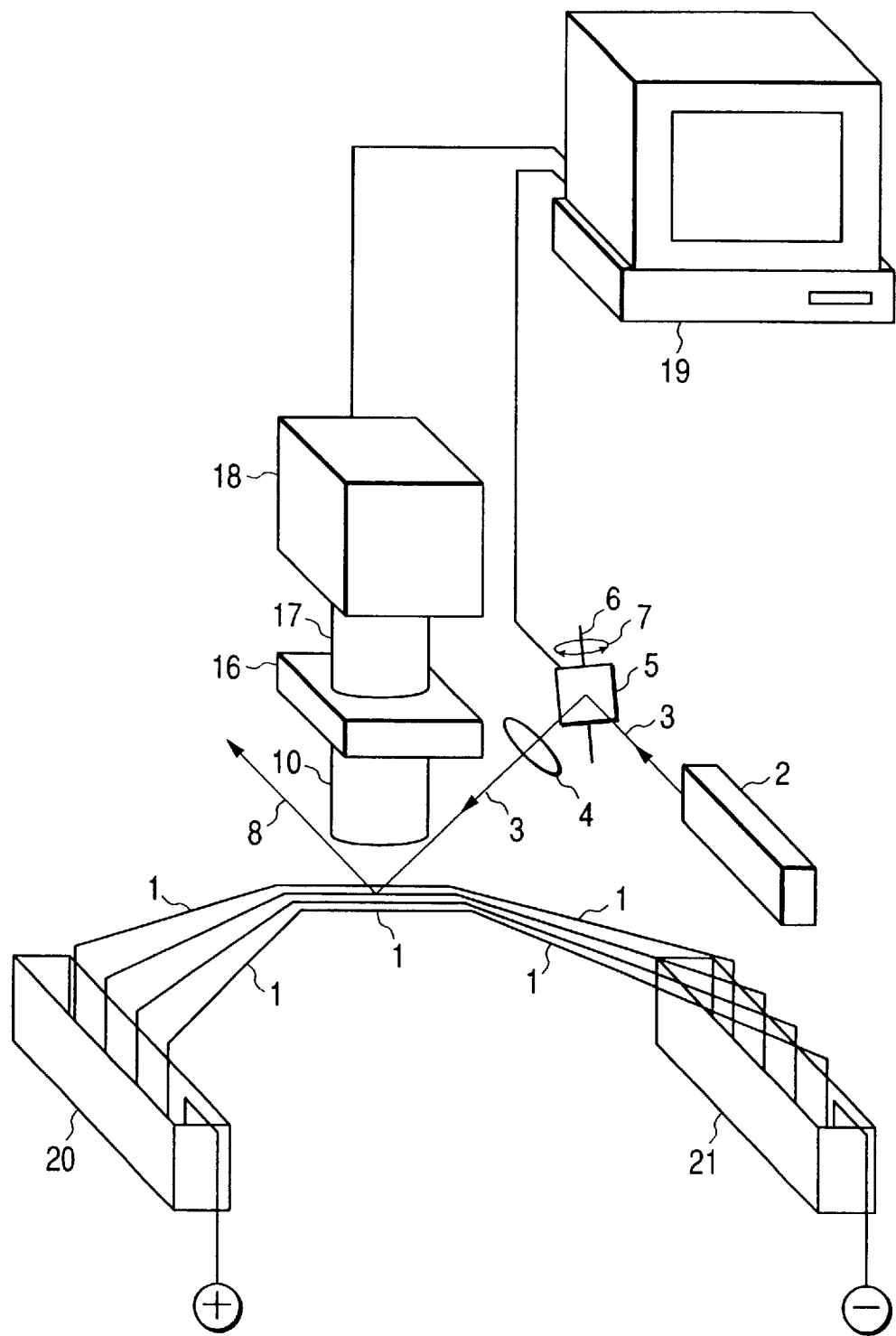
FIG. 9 is a diagram showing the overall construction of the capillary electrophoresis apparatus according to the embodiments of this invention.

FIG. 9 is a diagram showing the overall construction of the capillary electrophoresis apparatus in one embodiment of this invention. Fluorescence detection windows (which are irradiating positions of the laser beam 3 corresponding to the fluorescence detecting parts) are provided at positions respectively distant by 30 cm from the sample injection end in four capillaries 1 having an outer diameter of 360 μm, inner diameter of 50 μm and overall length of 50 cm, which are arranged as shown in FIG. 9.

The fluorescence detecting parts of the capillaries 1 are arranged close to one another horizontally on the same plane. The interval between the capillaries 1 widens towards the two ends of the capillaries 1, and the two ends are each immersed in buffer solution tanks 20, 21. The sample injection end is immersed in the buffer solution tank 21 as the negative pole, and the electrophoresis end point is immersed in the buffer solution tank 20 as the positive pole. A high voltage is applied to both ends of the capillaries 1, and electrophoresis is performed from the buffer solution tank 21 to the buffer solution tank 20.

To excite a sample labeled by a fluorephore moving electrophoretically inside the capillaries 1, the laser beam 3 emitted by the laser source 2 is reflected by the galvanomirror 5, converged by the light collecting lens 4, and irradiated to the position of the fluorescence detecting window from the direction of 45° to the plane in which the capillaries are disposed. The axis 6 of the galvanomirror 5 is rotated back and forth in the rotational direction 7 so that the laser beam 3 scans and repeatedly irradiates the fluorescence detecting positions of the capillaries 1 in sequence. The rotation angle of the galvanomirror 5 is controlled by a computer 19. The fluorescent light emitted from the fluorescence detecting positions of the capillaries 1 is detected independently and simultaneously by a fluorescence detection system 10–18 positioned vertically above the plane in which the fluorescence detecting positions of the capillaries 1 are aligned.

The fluorescence from the capillaries 1 is rendered effectively parallel by the objective lens 10, passed through an image splitting prism and spectral filters 16, brought to an image by an image-forming lens 17, and detected by a CCD camera 18. In the image splitting prism and spectral filters 16, the light from one point is split into four points by the prism, and the split light from the point is passed through four different band pass filters. By measuring the fluorescence intensity of four points simultaneously using the CCD camera 18, the fluorescence intensity of four different fluorescent materials can be measured simultaneously. The computer 19 controls repeated fluorescence measurements by the CCD camera 18, records the data obtained, and performs desired computational processing.

What is claimed is:

1. A capillary array electrophoresis apparatus comprising:
   plural capillaries for separating fluorephore-labeled samples by electrophoresis, said plural capillaries being arranged in a same plane;
   a laser source for irradiating said plural capillaries;
   means for scanning a laser beam from the laser source;
   a fluorescence detecting system which detects fluorescence emitted by said fluorephore-labeled samples, the fluorescence detecting system having a lens to collect said fluorescence from said capillaries and being fixed during the electrophoresis,
   wherein the relation $\theta_0 < \theta_3 - \tan^{-1}(D/2d)$ is satisfied where,
   $\theta_0$ ($\leq 90°$) is a maximum value of an angle between said laser beam and said same plane,
   $\theta_3$ ($\leq 90°$) is an angle between a central axis of said lens and said same plane,
   D is the diameter of entrance aperture of said lens,
   and d is the minimum distance between the center position of entrance aperture of said lens and position of said capillaries to be irradiated.

2. A capillary array electrophoresis apparatus according to claim 1, wherein said lens is an objective lens, and wherein the relation d=f is satisfied, where f is a working distance of said objective lens.

3. A capillary array electrophoresis apparatus according to claim 1, wherein said position of said capillaries to be irradiated is surrounded by a transparent liquid or transparent solid.

4. A capillary array electrophoresis apparatus comprising:
   plural capillaries for separating fluorephore-labeled samples by electrophoresis, said plural capillaries being arranged in a same plane;
   a laser source for irradiating said plural capillaries;
   means for scanning a laser beam from the laser source;
   a fluorescence detection system which detects fluorescence emitted by said fluorephore-labeled samples, the fluorescence detection system having a lens to collect said fluorescence from said capillaries and being fixed during the electrophoresis;
   wherein the relation $\theta_0 < 180° - \theta_3 - \tan^{-1}(D/2f)$ is satisfied, where
   $\theta_0$ ($\leq 90°$) is a maximum value of an angle between said laser beam and said same plane,
   $\theta_3$ ($\leq 90°$) is an angle between a central axis of said lens and said same plane,
   D is the diameter of entrance aperture of said lens, and
   f is a working distance of said lens.

5. A capillary array electrophoresis apparatus according to claim 4, wherein said position of said capillaries to be irradiated is surrounded by a transparent liquid or transparent solid.

6. A capillary array electrophoresis apparatus comprising:
   plural capillaries for separating fluorephore-labeled samples by electrophoresis, said plural capillaries being arranged in a same plane;
   a laser source for irradiating said plural capillaries;
   means for scanning a laser beam from the laser source;
   a fluorescence detection system which detects fluorescence emitted by said fluorephore-labeled samples, the fluorescence detection system having a lens to collect said fluorescence from said capillaries and being fixed during the electrophoresis;
   wherein the relation $\theta_0 > \theta_3 + \tan^{-1}(D/2d)$ is satisfied, where
   $\theta_0$ ($\leq 90°$) is a maximum value of an angle between said laser beam and said same plane,
   $\theta_3$ ($\leq 90°$) is an angle between a central axis of said lens and said same plane,
   D is the diameter of entrance aperture of said lens, and
   d is the minimum distance between the center position of entrance aperture of said lens and position of said capillaries to be irradiated.

7. A capillary array electrophoresis apparatus according to claim 6, wherein said lens is an objective lens, and wherein the relation d=f is satisfied, where f is a working distance of said objective lens.

8. A capillary array electrophoresis apparatus according to claim 6, wherein said position of said capillaries to be irradiated is surrounded by a transparent liquid or a transparent solid.

9. A capillary array electrophoresis apparatus comprising:
   plural capillaries for separating fluorephore-labeled samples by electrophoresis, said plural capillaries being arranged in a same plane;
   a laser source for irradiating said plural capillaries;
   means for scanning a laser beam from the laser source; and
   a fluorescence detection system which detects fluorescence emitted by said fluorephore-labeled samples, having a lens to collect said fluorescence from said capillaries,
   wherein said fluorescence detection system is fixed during the electrophoresis.

10. A capillary array electrophoresis apparatus according to claim 9, wherein said lens is an objective lens.

* * * * *